United States Patent [19]
Komine et al.

[11] Patent Number: 6,066,229
[45] Date of Patent: May 23, 2000

[54] METHOD OF RECYCLING DISK RECORDING MEDIUM AND APPARATUS FOR RECOVERING METAL REFLECTIVE FILM

[75] Inventors: Tetsuya Komine, Kanagawa; Hidemi Tomita, Tokyo; Mari Ichimura, Kanagawa, all of Japan

[73] Assignee: Sony Corporation, Tokyo, Japan

[21] Appl. No.: 09/112,227

[22] Filed: Jul. 9, 1998

Related U.S. Application Data

[60] Provisional application No. 60/052,449, Jul. 14, 1997.

[30] Foreign Application Priority Data

| Jul. 10, 1997 | [JP] | Japan | 9-185396 |
| Jul. 22, 1997 | [JP] | Japan | 9-195626 |
| Jul. 22, 1997 | [JP] | Japan | 9-195627 |

[51] Int. Cl.[7] .................................................. B32B 35/00
[52] U.S. Cl. .............................. 156/344; 156/584; 134/1
[58] Field of Search ..................... 156/344, 584; 264/36.1, 36.18; 134/1

[56] References Cited

U.S. PATENT DOCUMENTS

| 5,220,754 | 6/1993 | Tayebi et al. | 451/59 |
| 5,306,349 | 4/1994 | Nee | 134/1 |
| 5,445,555 | 8/1995 | Tokura et al. | 451/28 |
| 5,520,865 | 5/1996 | Sargent, III et al. | 264/106 |
| 5,619,898 | 4/1997 | Witt | 83/870 |

*Primary Examiner*—Mark A. Osele
*Attorney, Agent, or Firm*—Ronald P. Kananen; Rader, Fishman & Grauer PLLC

[57] ABSTRACT

A method of recycling a disk recording medium includes the steps of retaining the disk recording medium in a liquid medium, the disk recording medium having a layered structure including a substrate, a dye layer, a reflective film, and a protective layer; radiating ultrasonic waves onto the disk recording medium such that the substrate and the reflective film are separated from each other; and bringing a solution into contact with the substrate separated from the reflective film such that the dye layer is separated from the substrate in order to recover the substrate, the solution dissolving the dye layer.

8 Claims, 15 Drawing Sheets

6,066,229

METHOD OF RECYCLING DISK RECORDING MEDIUM AND APPARATUS FOR RECOVERING METAL REFLECTIVE FILM

This application claims the benefit of U.S. Provisional Application Ser. No. 60/052,449 filed Jul. 14, 1997.

BACKGROUND OF THE INVENTION

1. Field of the Invention

The present invention relates to a method of recycling a disk recording medium which has a layered structure including a substrate, a dye layer, a reflective film, and a protective layer.

2. Description of the Related Art

Disk recording media, such as optical disks, have been widely used, for example, for recording music, images, and information because of their capability of high-density recording. In particular, compact disks (CDs) and other optical disks in the CD family have been used on a large scale.

Under the present circumstances, with regard to the issue of waste, the recycling of optical disks such as compact disks is being investigated. Most optical disks on the market are read-only type, such as CDs. As shown in FIG. 1, for example, a CD includes a polycarbonate substrate L3, an aluminum reflective film L2, and a protective layer L1 deposited in that order.

In a conventional method of recycling disks, disks are crushed as they are and molded. In such a case, the components of the protective layers and reflective films are also mixed into the molded product. It is not possible to recover the reflective films only, and the molded product is not transparent. Thus, the molded product is applicable only for limited usage.

In another method, disks are immersed in an acid or an alkaline solution to dissolve aluminum reflective films, thereby protective layers and substrates are separated from each other, and thus, the substrate resin is recycled. In this method, the recycled substrates are transparent and can be reused in a relatively wide usage, however, it is difficult to recover reflective films.

Apart from the read-only disks, recordable optical disks are also on the market. Although there are several types that are recordable, the present invention relates to optical disks which have a layered structure, as shown in FIG. 2, including a substrate L7, a dye layer L6, a reflective film L5 and a protective layer L4. Generally, in this type, recording is allowed only once. An example of this type is a CD-R (recordable compact disk). The CD-R includes, for example, a polycarbonate substrate, additives such as an organic dye, for example, a cyanine dye, and a quencher, a gold reflective film, and an ultraviolet-curable resin such as an acrylic resin.

Also, there is a DVD-R (recordable high-density recording disk: digital video disk), in which two layered structures described above are laminated together by means of, for example, an adhesive as shown in FIG. 3. That is, protective layers L11 and L11 are adhered together with an adhesion layer B. and a dye layer L9, a gold reflective film L10, and a protective layer L11 are deposited on a substrate L8 in that order on both sides. In these types of disks, in addition to substrates, expensive gold reflective films are used, and thus, the recovery of reflective films has been desired. For that purpose, although it may be possible to use a solution which dissolves reflective films as described above, only an extremely hazardous solution, for example, aqua regia, can be used. Also, by treating the whole disks at high temperature, organic substances such as substrates are burnt and gold only can be recovered, however, in this method, the substrate resin cannot be recovered.

The optical disks described above, shown in FIG. 2 and FIG; 3, have a layered structure including substrates, dye layers, reflective films, and protective layers. There is a need for recovering the substrates, the dye layers, and the reflective films separately. In particular, if the dye components of the dye layers are not recovered separately from the substrates, the resinous substrates cannot be recycled.

SUMMARY OF THE INVENTION

It is an object of the present invention to provide a method of recycling disk recording media, in which the substrates, the reflective films, and the dye components are separated and at least the substrates are securely recovered for recycling.

In order to achieve the object described above, in accordance with the present invention, a method of recycling a disk recording medium, which has a layered structure including a substrate, a dye layer, a reflective film, and a protective layer, includes the steps of radiating ultrasonic waves onto the disk recording medium in a liquid medium such that the substrate and the reflective film are separated from each other, and bringing a solution which dissolves the aye layer into contact with the substrate such that a dye component is separated in order to recover the substrate.

In accordance with the present invention, first, the substrate and the reflective film are separated from each other by radiating ultrasonic waves, in a liquid medium, onto the disk recording medium which has a layered structure including the substrate, the dye layer, the reflective film, and the protective layer. Then, the substrate is brought into contact with a solution which dissolves the dye layer. Thus, the dye component is removed, and the pure substrate component alone can be recovered.

Accordingly, the substrate can be recovered purely, excluding the dye component and the reflective film.

Also, in accordance with the present invention, preferably, by notching at least the protective layer between the protective layer and the reflective film when the substrate and the reflective film are separated from each other by ultrasonic radiation in a liquid medium, at least the separation speed of the protective layer can be accelerated, and efficiency in separation and recovery with respect to the substrate and the reflective film can be enhanced.

Also, in accordance with the present invention, preferably, by heating the separated reflective film to recover the reflective film, efficient recovery of the reflective film can be performed.

Also, in accordance with the present invention, preferably, by adding a solution that dissolves the dye layer onto the substrate, the dye component is separated from the resinous substrate while the substrate and the reflective film are separately recovered. Thus, the resinous substrate component can be recovered separately from the dye layer.

DESCRIPTION OF THE PREFERRED EMBODIMENTS

The preferred embodiments of the present invention will be described in detail with reference to the attached drawings.

While various technically preferred limitations are placed on the preferred embodiments described below, it is to be understood that the scope of the invention is not limited to the disclosed embodiments unless there is a mention of limitations.

Figure 4:
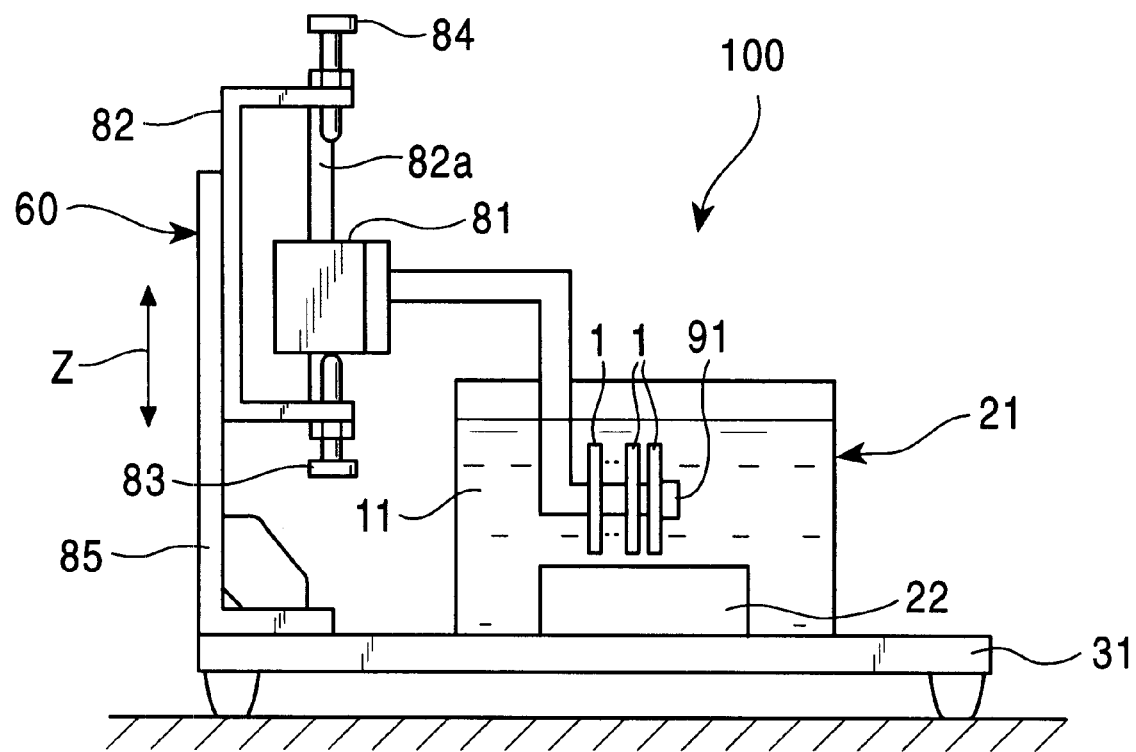
FIG. 4 shows a recycle apparatus as a preferred embodiment for performing a method of recycling disk recording media in accordance with the present invention.

First, FIG. 4 shows an example of a recycle apparatus for carrying out a preferred embodiment of a method of recycling disk recording media in accordance with the present invention.

A recording medium (hereinafter referred to as a disk) 1 to be treated with a recycle apparatus 100 shown in FIG. 4 will be briefly described with reference to FIG. 5. the disk 1 is, for example, a CD-R (recordable compact disk) which is an optical disk, and has a layered structure including a polycarbonate substrate 1d, a recording dye layer (dye layer) 1c, a gold reflective layer (reflective layer) 1b as a metal reflective film, and a top-coat layer 1a composed of UV-curable (ultraviolet-curable) resin. Guide grooves 1e are provided in the polycarbonate substrate 1d.

If the gold reflective layer 1b can be separated from the polycarbonate substrate 1d in the disk 1 with the recycle apparatus 100, the gold reflective layer 1b will be recycled, and also the scope of the recycling of the polycarbonate substrate 1d will broaden.

The recycle apparatus 100 includes, an ultrasonic cleaning bath 21 as a container, an operation unit 60, an ultrasonic generator 22 as a vibration means, a base 31. and the like.

A mounting plate 85 of the operating unit 60 is perpendicularly fixed onto the base 31. The ultrasonic cleaning bath 21 is preferably set in a detachable manner or fixed onto the base 31 near the mounting plate 85. The ultrasonic cleaning bath 21 contains a given amount of water 11 as a medium. The ultrasonic generator 22 is placed on the inner bottom of the ultrasonic cleaning bath 21.

The operation unit 60 is a device for placing a disk or a plurality of disks 1 in water 11 within the ultrasonic cleaning bath 21, and retrieving the disks 1 out of water 11 after the gold reflective layer 1b is recovered.

An air table cylinder 82 as a drive means is assembled into the mounting plate 85 of the operation unit 60. An upper-end stopper 84 is fixed on the top end of the air table cylinder 82, and a lower-end stopper 83 is mounted on the bottom end of the cylinder 82.

A movable table 81 is moved along a rod 82a in the Z direction (vertically) by means of air pressure.

Figure 6:
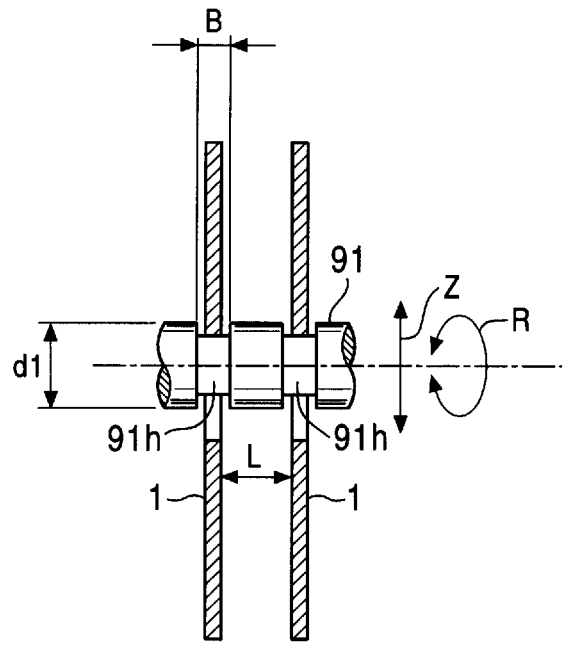
FIG. 6 shows a state in which a cleaning device of the apparatus shown in FIG. 4 retains a plurality of disks.

A cleaning device (retainer) 91 is mounted on the movable table 81. The cleaning device 91 detachably retains a disk or a plurality of disks 1. FIG. 6 shows a portion of the cleaning device 91, and grooves 91h are formed at a given distance L along the cleaning device 91 (in FIG. 6, for example, two grooves 91h are shown). A maximum diameter d1 of the cleaning device 91 is set smaller than an inside diameter of the disk 1 such that the cleaning device 91 can be inserted into a center hole of the disk 1.

Each of the grooves 91h places a portion which constitutes a center hole of the disk 1. The disk 1 can be moved very short distances in the Z direction; moved along the axis of the cleaning device 91, or rotated in the direction R of rotation.

As the water 11 shown in FIG. 4, for example, pure water or tap water may be used.

Figure 7:
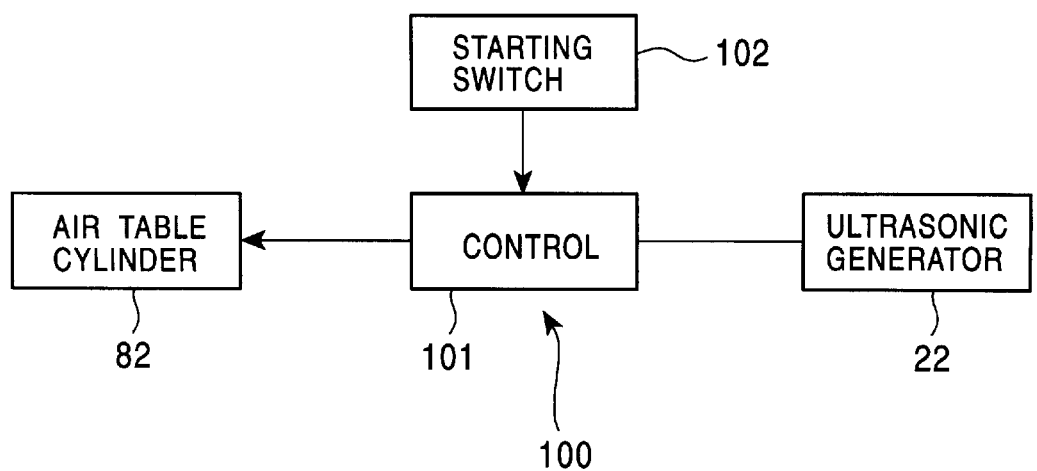
FIG. 7 shows a control block diagram of the recycle apparatus shown in FIG. 4.

FIG. 7 schematically shows a control block diagram of the recycle apparatus 100 shown in FIG. 4. A control 101 is connected to a starting switch 102, the air table cylinder 82, the ultrasonic generator 22, and so on.

Figure 8:
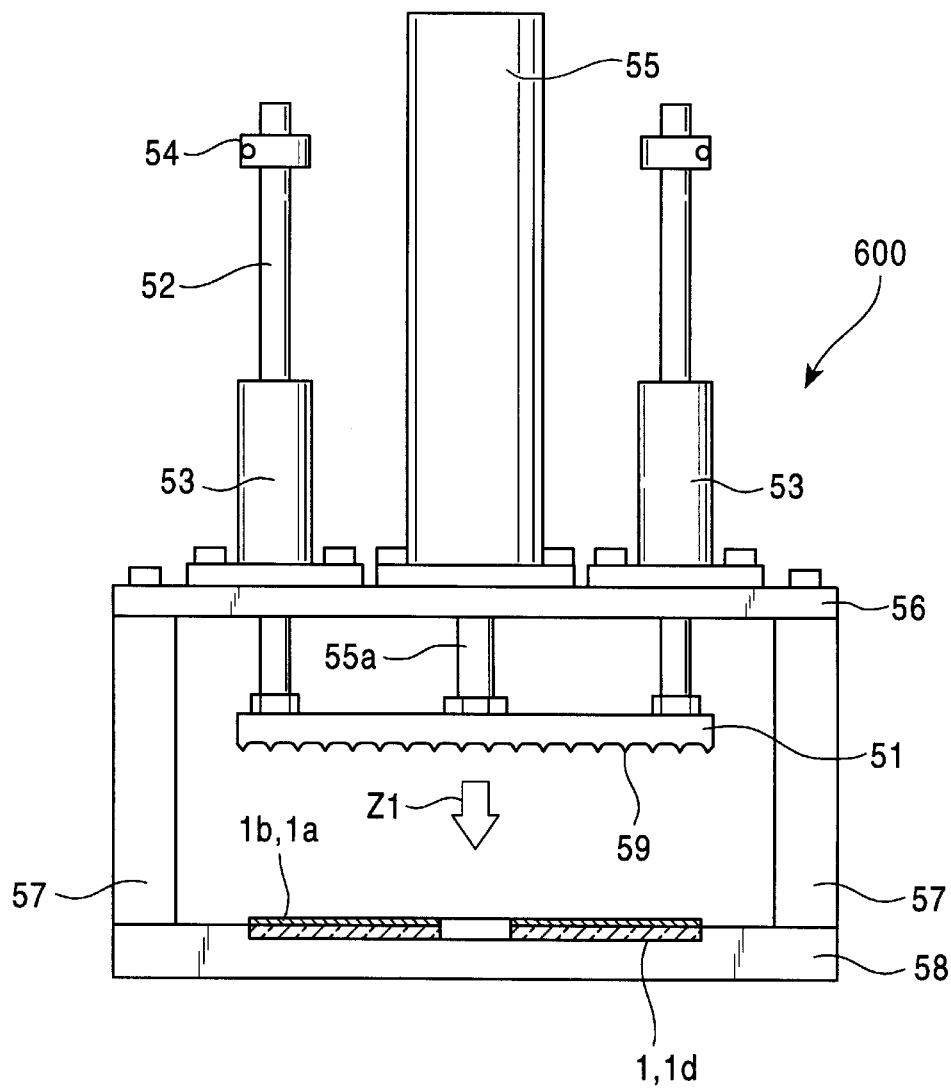
FIG. 8 shows an example of a notching means for notching at least a protective layer in a disk.

Next, FIG. 8 will be referred to.

A notching means 600 shown in FIG. 8 actively notches, preferably, the gold reflective layer 1b and the UV-curable resin top-coat 1a in the disk 1, or at least, the UV-curable resin top-coat 1a. The notching means 600 is an apparatus for making notches before recycling treatment is performed to the gold reflective layer 1b and the UV-curable resin top-coat layer 1a in the disk 1 by means of the recycle apparatus 100 shown in FIG. 4.

In accordance with the embodiment shown in FIG. 4, a used disk, a defective disk during production process, or an unused disk is mounted as it is on the cleaning device 91, and the gold reflective layer 1b and the UV-curable resin top-coat layer 1a in the disk 1 are separated and recovered.

Figure 9:
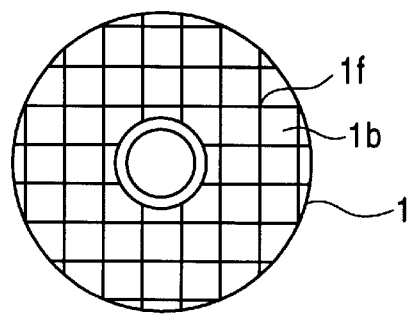
FIG. 9 shows an example of notches made with the notching means.

On the other hand, the notching means 600 shown in FIG. 8 is used so that recovery efficiency of the gold reflective layer in accordance with the recycle apparatus 100 shown in FIG. 4 can be enhanced by actively notching the gold reflective layer 1b and the UV-curable resin top-coat layer 1a, in advance, with a pattern shown in FIG. 9.

The notching means 600 includes a positioning section 58, a setting plate 56, a supporting plate 57, two linear guides 53 and 53, and a metal mold 51.

The metal mold 51 is fixed on the bottom ends of the linear shafts 52 and 52 of the linear guides 53 and 53. Also the center of the metal mold 51 is fixed on a rod 55a of an air cylinder 55.

The disk 1 is positioned so that the gold reflective layer 1b and the UV-curable resin top-coat 1a beneath the label surface are opposed to the metal mold 51.

Several protruding portions 59 for making grooves are formed on the bottom surface of the metal mold 51. The protruding portions 59 are shaped such that, for example, a notch pattern 1f shown in FIG. 9 is made on the label surface side of the disk 1.

When the cylinder 55 of the notching means 600 is in operation, the metal mold 51 moves downward in the Z1 direction along the linear guides 53 and 53, and thereby, the pattern shown in FIG. 9 can be notched onto the gold reflective layer 1b and the UV-curable resin top-coat 1a on the label surface side of the disk 1.

As described above, by preliminarily making notches onto the gold reflective layer 1b and the UV-curable resin top-coat 1a with the protruding portions 59 (edges) of the metal mold 51, the separation and recovery of the gold refleotive layer 1b can be performed in a shorter period of time by using the recycle apparatus 100 shown in FIG. 4.

In accordance with the embodiments of the present invention, a disk is irradiated with ultrasonic waves in water as it is, or after notches are made onto the reflective layer 1b and the top-coat layer 1a with the notching means 600 as shown in FIG. 8, or after the disk is crushed. At this stage, there is no particular condition of intensity with respect to ultrasonic frequency generating from the ultrasonic generator 22 shown in FIG. 4, and frequencies of approximately 24 to 28 kHz which can be generated by a typical ultrasonic vibrator are suitable. With a lower frequency than the above, higher efficiency will be obtained, however, a more expensive device is required. Also, if energy density caused by ultrasonic vibration is 0.5 W/cm$^2$ or more, efficient separation can be performed. Also, a single disk, or a plurality of disks at the same time, may be treated.

Regardless of whether ultrasonic treatment is performed during or after, water as a medium may be circulated, and by the circulation, separation can be accelerated, and resticking of the separated reflective films and the like onto the substrate can be prevented.

Also, if notches are made on the side of the protective layer (top-coat layer 1a) of the disk before ultrasonic radiation, the separation of the refleotive film 1b is accelerated, which is very effective. There is no particular condition with respect to a notching means, and instead of the edges (protruding portions 59) shown in FIG. 8, an electrically heated wire or a laser beam may be used. Although the depth, position, and number of notches do not have any limitations, the most preferable depth is that which extends from the protective layer side onto the dye layer.

Water, as the medium during ultrasonic radiation, does not necessarily have high purity, and may have additives as required. For example, by adding a surfactant into water, separation is accelerated, water is effectively drained after treatment, and reflective films are prevented from sticking to disks again. Also, there is no particular condition of temperature during ultrasonic radiation, and good results are obtainable at room temperature.

In accordance with ultrasonic treatment described above, the optical disk is divided into the substrate, and the reflective film and the protective layer.

Next, a method of recycling in accordance with the recycle apparatus 100 shown in FIG. 4 will be described with reference to FIG. 4 and FIG. 6.

With the movable table 81 elevated, a disk or a plurality of disks 1 are fitted into the grooves 91h on the cleaning device 91 as shown in FIG. 6. At this stage, the faces of the disks 1 lie substantially in the Z direction (perpendicularly), and are positioned at a given distance L. Also, the width B of the groove 91h is larger than the thickness of the disk 1. Therefore, the disk 1 on the cleaning device 91 is rotatable in the directions R of rotation, and vertically movable in the Z direction, and also, the disk 1 can be slightly moved along the axis of the cleaning device 91.

Next, the movable table 81 is lowered by means of the cylinder 82. With the table 81 lowered, the disks 1 are completely immersed in water 11.

When the starting switch 102 shown in FIG. 7 is pressed by an operator, the control 101 starts the ultrasonic generator 22. By activating the ultrasonic generator 22, for example, at a frequency of 26 kHz, with an output of 600 W, for approximately 10 seconds, the UV-curable resin top-coat layer 1a and the gold reflective layer 1b are separated from the polycarbonate substrate 1d in the disk 1 shown in FIG. 5.

The separation (cleaning) mechanism is generally considered to include two actions. One is cavitation caused by vibration, and the other is physical and chemical reaction acceleration. In accordance with the embodiment of the present invention, einoe water is used as a medium, there is little chemical reaction acceleration.

In general, when an ultrasonic wave perpendicularly enters into, for example, a rigid body, a wave that does not travel occurs because of overlapping of an incident wave and a reflected wave. This is referred to as a standing wave. Under the influence of the standing wave, uneven separation (cleaning) occurs. In order to prevent the unevenness, the disk 1, being an object to be cleaned, is vertically moved or rotated in water 11, being a medium, during cleaning.

In accordance with the embodiment of the present invention, in particular, by using the axial cleaning device 91 which has a clearance under the center hole of the disk 1, the flow caused by water 11, as the medium, rotates the disk 1, thus, preventing the uneven separation.

The ultrasonic generator 22 is stopped, and the movable table 81 is elevated. With the movable table 81 elevated, the disk 1 is retrieved from the cleaning device 91.

Figure 5:
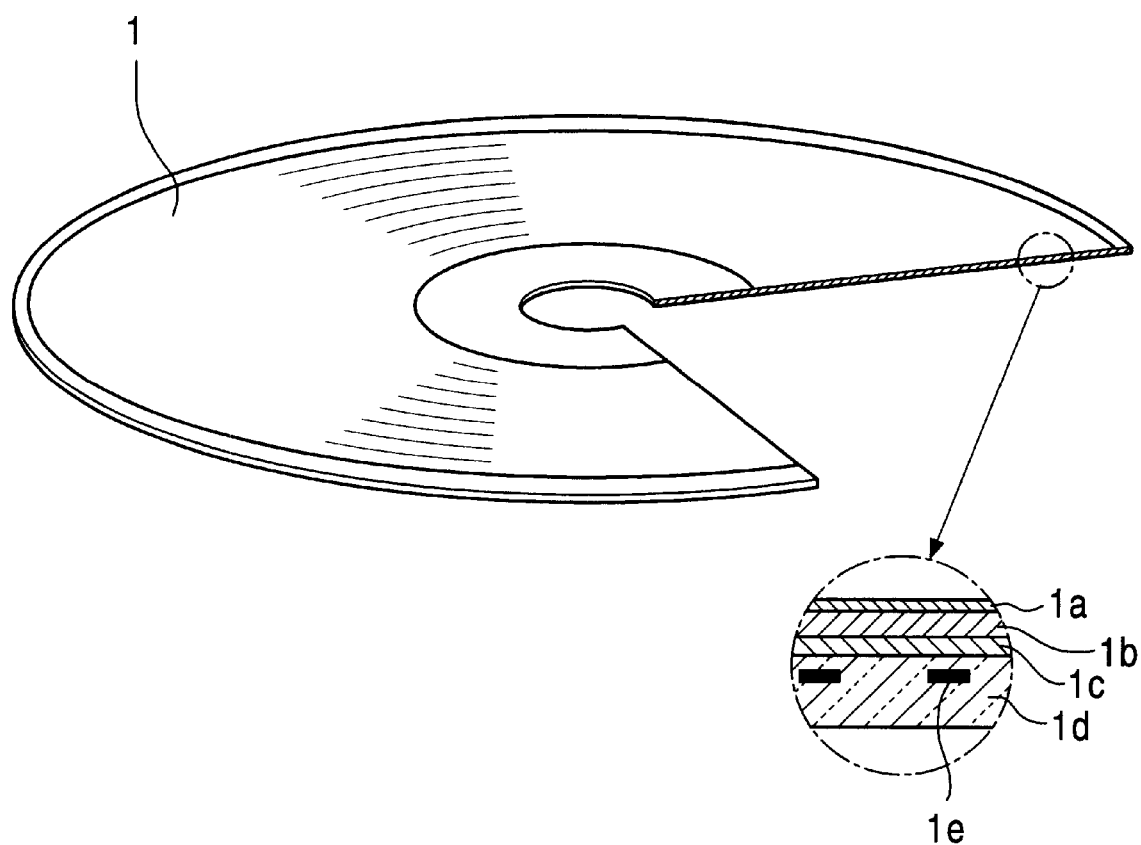
FIG. 5 shows an example of a disk to be recycled.

The disk 1 from which the gold reflective layer 1b and the UV-curable top-coat layer 1a have been separated includes the recording dye layer 1c and the polycarbonate substrate 1d as shown in FIG. 5. The UV-curable resin top-coat layer 1a and the gold reflective layer 1b float or sink in the water 11 after the separation.

The top-coat layer 1a and the gold reflective layer 1b can easily be separated from the water as the medium by means of a net or the like. The gold reflective layer 1b is recycled as a valuable material.

Although the ultrasonic generator is operated only when the disks are in water in accordance with the embodiment of the present invention, the ultrasonic generator may be activated at all times.

Although the recording dye layer 1c is attached onto the substrate 1d, the substrate resin can be used as a recycling material as it is by crushing or other treatment. However, if a dye component remains, coloring appears on the recycled resin, resulting in limitations on usage after recycling.

As a method of removing the recording dye layer 1c from the substrate 1d, immersion into a solvent which dissolves dyes, or spraying of the solvent are proposed.

Although there are no specific conditions required for a solvent to be used in the above method, a solvent that does not affect the polycarbonate of the substrate 1d, and that can dissolve the dye component may be used. For instance, an alcoholic solvent, for example, ethanol. methanol, isopropyl alcohol, and n-butyl alcohol; ethylene-1,2-diol and glycerin: a cellosolve solvent, for example, 2-methoxyethanol and 2-ethoxyethanol; and a hydroxyketone-based solvent, for example, 2-hydroxy-2-methyl-3-butanone, 4-hydroxy-2-butanone, and 4-hydroxy-4-methyl-2-pentanone, may be used.

Consequently, the recording dye layer 1c is dissolved, and the resin of the substrate 1d can be recycled as a transparent resin. In such a case, if a general-purpose solvent, for example, acetone or toluene, is used, the solvent is absorbed by the polycarbonate substrate, thus, resulting in difficulty in recycling the resin of the substrate 1d.

Also, a mixture of solvents may be used, and if at least a solvent described above is included, for example, by properly mixing ethanol with water, the object of the present invention can be achieved.

If the solvent described above is added to the water in the ultrasonic cleaning bath 21 shown in FIG. 4 during ultrasonic radiation to treat the disk 1, the dye layer can be removed from the substrate while the reflective film 1b is being separated from the substrate. There is no specific limit to the amount to be added, however, if the amount is too small, no effect is obtained, and if the amount is too large, the ultrasonic effect is reduced by half, and also there is a problem in view of handling an organic solvent. Therefore, preferably the amount ranges from 2% to 50%, and most preferably the amount ranges from 5% to 30%. Also, a mixture of solvents may be used.

Also, with respect to the separated metal reflective film 1b and the protective layer 1a shown in FIG. 6, the component of the protective film, which is an organic substance, is vaporized by high temperature treatment, and the metal component alone can be recovered. There is no specific method required for the high temperature treatment, and treatment with an oven or the like is possible. If the treatment temperature is higher than the melting point of the metal in the reflective film, the recovery of the metal will be facilitated.

Figure 10:
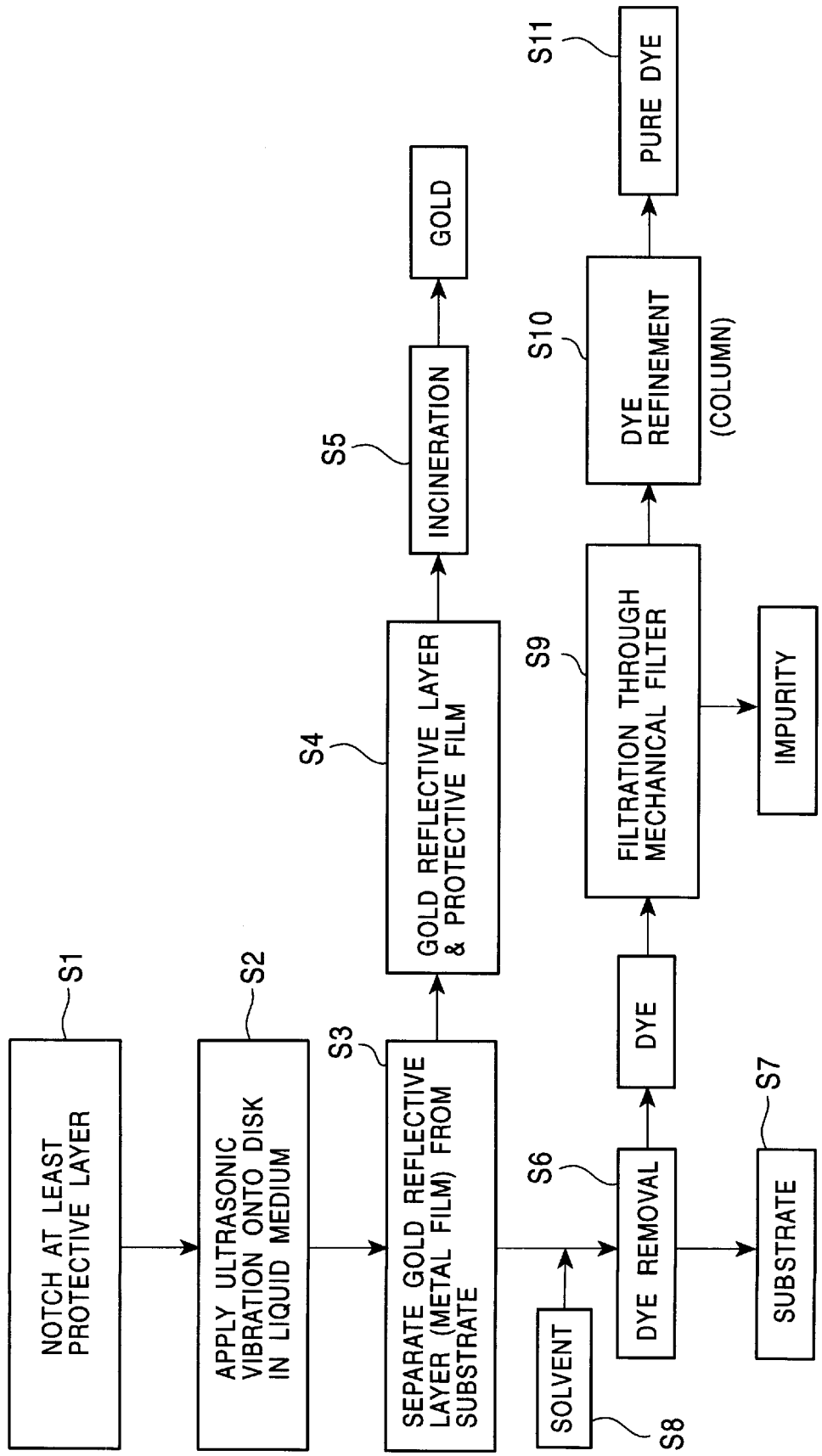
FIG. 10 is a flow chart showing an example of the method of recycling disk recording media in accordance with the present invention.

An example of the method of recycling disk recording media, which is described above, is shown in FIG. 10.

Step S1: Preferably notch at least the protective layer in the disk.

Step S2: Apply ultrasonic vibration to the disk in a liquid medium.

Step S3: Separate the gold reflective layer (metal film or metal layer) from the substrate.

Step S4: The gold reflective layer and the protective layer (protective film) separated from the substrate are obtained.

Step 5: Incinerate the gold reflective layer and the protective film by heating at a temperature that is nearly the melting point of the metal reflective layer, for example, at approximately 1,200° C., in order to remove the protective film from the gold refleotive layer, and thus, gold alone is obtained.

Steps S6, S7, and S8: Bring a solvent (shown in Step S8) into contact with the substrate, from which the gold reflective layer has been separated, in order to separate the dye, and recover, for example, the resinous substrate alone.

Step S9: Filter the dye obtained in Step S6 with, for example, a mechanical filter, to completely separate impurities from the dye.

Step S10: Refine the filtered dye in a column, and the pure dye is obtained in Step S11.

As described above, in Step S7 the polycarbonate substrate alone can be separated, in Step S5 pure gold alone can be obtained, and in Step S11 the pure dye can be obtained.

By recovering the resinous substrate to be recycled, it can be recycled, for example, as a material for substrates for disk recording media or the like. The recovered substrate may be pelletized to produce polycarbonate resin pellets.

In the following example, a CD-R disk (product number: CDQ-74A) manufactured by Sony Corporation was used as an optical disk including a substrate, a dye layer, a reflective film, and a protective film. As an ultrasonic generator (ultrasonio radiation apparatus) 22 used for the recycle apparatus 100 shown in FIG. 4, an ultrasonic cleaner (26 kHz, 600 W) manufactured by Kaijo Corporation was used. As a liquid medium, tap water was used.

(1) Ultrasonic waves were applied to a disk suspended in the cleaning bath for 10 minutes. The substrate having the dye, the protective film stuck to the metal film, and the metal powder of the reflective film were separated from each other. After taking the substrate out of the liquid, the liquid was filtered to remove the protective film stuck to the metal film, and the metal powder, which were left in the air to be dried.

(2) The protective layer side of a disk was notched, for example, with a razor, in a checkered shape having 1 cm checks. Next, the protective film and the metal powder of the reflective film were separated. After taking the substrate out of the liquid, the liquid was filtered to remove the protective film stuck to the metal film and the metal powder, which were left in the air to be dried. Instead of the razor, the notching means 600 shown in FIG. 8 may be used.

(3) A disk was cut by a cutter approximately 2 by 2 centimeters square, and ultrasonic waves were applied for five minutes while stirring. The substrate having the dye, the protective film stuck to the metal film, and the metal powder of the reflective film were separated from each other. After taking out the substrate resin from the liquid, the liquid was filtered to remove the protective film stuck to the metal film and the metal powder, which was left in the air to be dried.

(4) The protective films and metal portions recovered and dried in the methods (1) through (3) were treated for two hours at a temperature of 1,200° C. in an electric oven. As a result, gold as the reflective film metal was obtained.

(5) The substrate resin recovered in the methods (1) through (3) was immersed in the solvents described below for two minutes and then taken out. Dye dissolution and effect on the substrates are summarized in the following table.

TABLE 1

| Solvent | Dye Dissolution | Effect on Substrates |
| --- | --- | --- |
| Methanol | Observed | None |
| Ethanol | Observed | None |
| Isopropyl alcohol | Observed | None |
| N-butyl alcohol | Observed | None |
| Ethylene-1,2-diol | Observed | None |
| Glycerin | Observed | None |
| 2-methoxyethanol | Observed | None |
| 2-ethoxyethanol | Observed | None |

TABLE 1-continued

| Solvent | Dye Dissolution | Effect on Substrates |
|---|---|---|
| 2-hydroxy-2-methyl-3-butanone | Observed | None |
| 4-hydroxy-2-butanone | Observed | None |
| 4-hydroxy-4-methyl-2-pentanone | Observed | None |
| Acetone | Observed | Observed |
| Acetic acid 2-methoxyethyl ester | Observed | Observed |
| Ethanol/water (80/20) | Observed | None |

TABLE 2

| Solvent | Dye Dissolution | Effect on Substrates |
|---|---|---|
| N-hexane | None | None |
| Water | None | None |

TABLE 3

| Solution Composition | Dye Dissolution |
|---|---|
| Water/Ethanol (99/1) | Partially observed |
| Water/Ethanol (95/5) | Observed |
| Water/Ethanol (80/20) | Observed |
| Water/Ethanol (60/40) | Observed |
| Water/Ethanol (40/60) | Observed |
| Water/Methanol (99/1) | Partially observed |
| Water/Methanol (95/5) | Observed |
| Water/Methanol (80/20) | Observed |
| Water/Methanol (60/40) | Observed |
| Water/Methanol (40/60) | Observed |
| Water/Ethanol (100/0) | None |

The solvents presented in TABLE 1 dissolve dyes, and do not affect substrates excluding acetone and acetic acid 2-methoxyethyl ester. However, n-hexane and water presented in TABLE 2 do not dissolve dyes. Also, solutions having the composition presented in TABLE 3 dissolve dyes, excluding water/ethanol (10%).

[0032]
The present invention is applicable not only to CDs (compact disks) and CD-Rs but also to other types of optical disks and magneto-optical disks, for example, digital video disks (DVDs) and laser disks (LDs).

In the embodiments shown in FIG. 4, FIG. 8 and the like, the disks 1, in parallel to each other, are substantially vertically retained with the cleaning device, however, the individual disks may be retained obliquely in relation to the vertical direction, or another retaining method may be used. Also, a single disk or a plurality of disks may be retained with the cleaning device.

Figure 1:
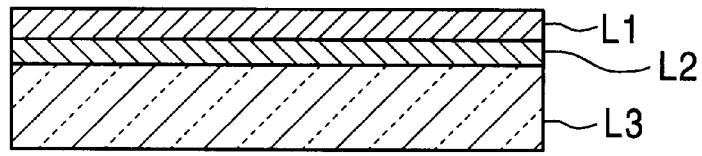
FIG. 1 shows an example of a disk recording medium.
Figure 2:
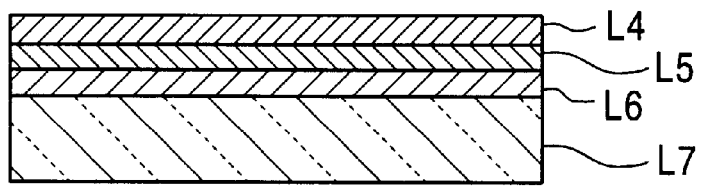
FIG. 2 shows an example of a disk recording medium.
Figure 3:
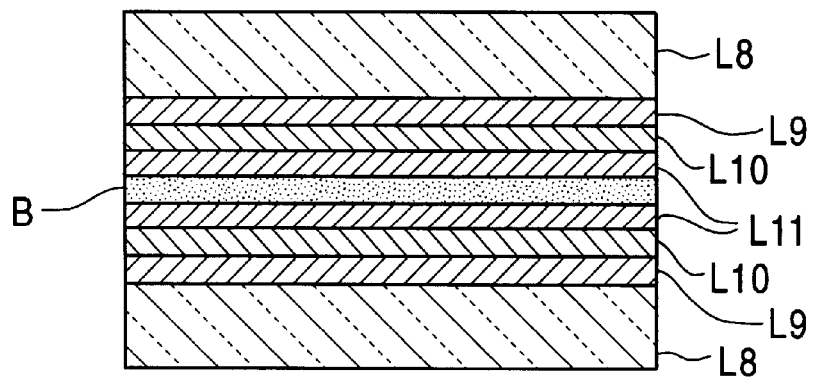
FIG. 3 shows an example of a disk recording medium.

The method of recycling disk recording media in accordance with the present invention is of course applicable to a disk recording medium having the structure shown in FIG. 1. The disk recording medium shown in FIG. 3 is a so-called "high density recording disk" and is referred to as a DVD (digital video disk), in which a substrate having a similar structure is deposited with an adhesion layer B therebetween. The adhesion layer B adheres the protective layers L11 and L11, and a dye layer L9, a reflective film L10, and a protective layer L11 are deposited on each substrate L8 in that order.

Although ultrasonic vibration from an ultrasonic generator is used in order to vibrate disks, other types of vibration generator may be employed.

Next, another embodiment of the present invention will be described with reference to FIG. 11 and FIG. 12.

Figure 11:
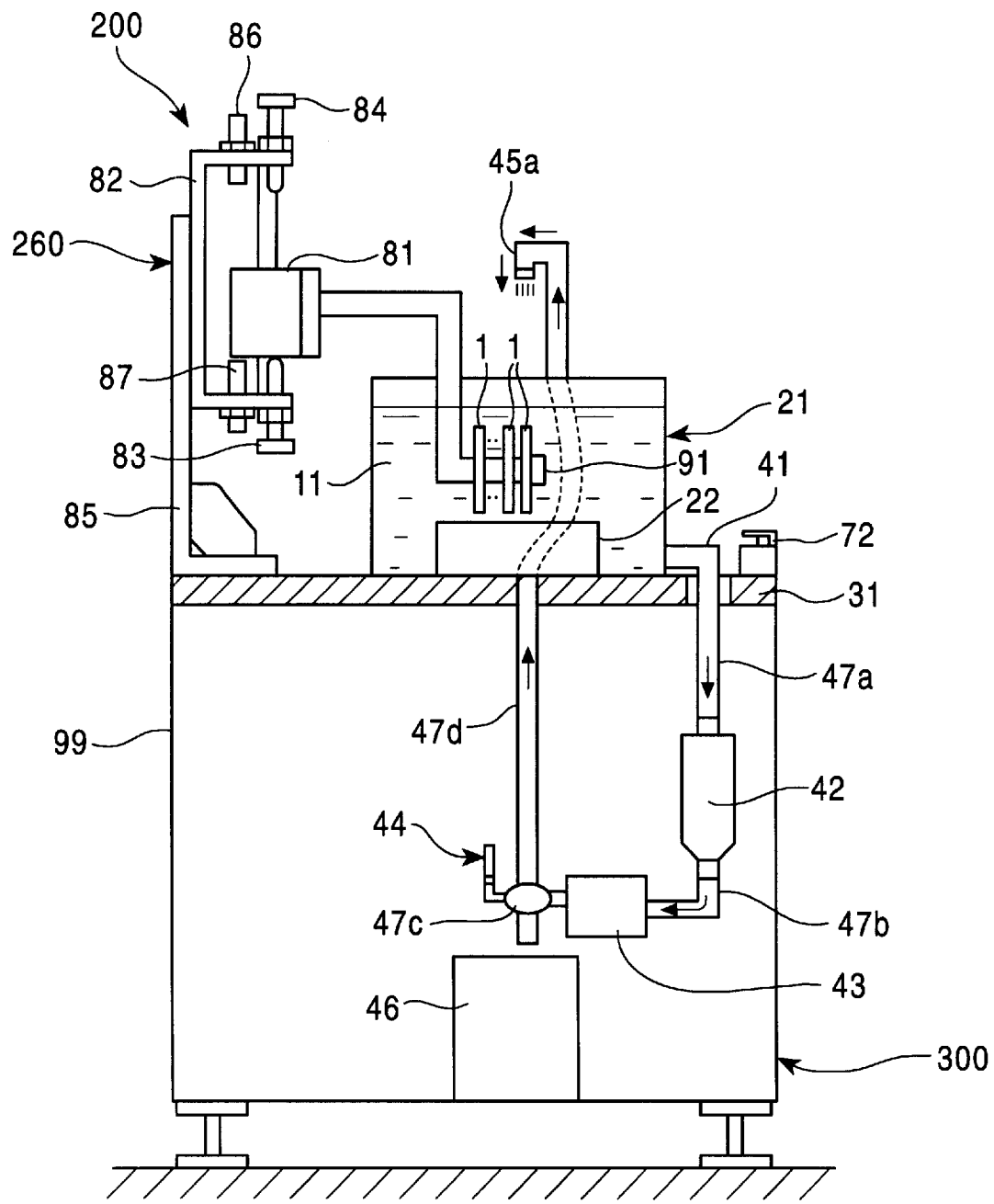
FIG. 11 shows an apparatus for recovering metal reflective films as an embodiment of the present invention.

An apparatus for recovering metal reflective films 200 shown in FIG. 11 includes sensors 86 and 87, a metal reflective film removal means 300, and a nozzle 45a as a fluid spray means, in addition to the units of the recycle apparatus 100 shown in FIG. 4.

The apparatus for recovering metal reflective films 200 includes an ultrasonic cleaning bath 21 as a container, an ultrasonic generator 22 as a vibration means, an operation unit 260, the metal reflective film removal means 300, and the nozzle 45a as a fluid spray means.

The ultrasonic cleaning bath 21 is detachably set or fixed on a base 31, and a mounting plate 85 of the operation unit 260 is also perpendicularly fixed on the base 31. A cylinder (drive means) 82 of the operation unit 260 detects a stop position of a movable table 81 in response to signals from an upper-end sensor 86 and a lower-end sensor 87.

The ultrasonic generator 22 is provided on the inner bottom of the ultrasonic cleaning bath 21, and a water outlet 41 is provided thereabout. The metal reflective film removal means 300 is provided between the water outlet 41 and the nozzle 45a.

The metal reflective film removal means 300 is contained in a support 99. The water outlet 41 is connected to a mechanical filter 42 with a pipe 47a therebetween. An outlet of the mechanical filter 42 is connected to a pump 43 with a pipe 47b therebetween. An outlet of the pump 43 is connected to a directional valve 44 with a pipe 47c therebetween. One of the outlets of the directional valve 44 is connected to the nozzle 45a with a pipe 47d therebetween. The other outlet of the directional valve 44 is directly above a discharge container 46.

When the water 11 as the medium is exchanged, the water is received into the discharge container 46 by switching over the directional valve 44. The nozzle 45a lies above the ultrasonic cleaning bath 21.

When the separation and the recovery of metal reflective films are performed, the water 11 in the ultrasonic cleaning bath 21 circulates among the ultrasonic cleaning bath 21, the outlet 41, the pipe 47a, the mechanical filter 42, the pipe 47b, the pump 43, the pipe 47c, the directional valve 44, the pipe 47d, the nozzle 45a, and the ultrasonic cleaning bath 21, in that order.

Figure 12:
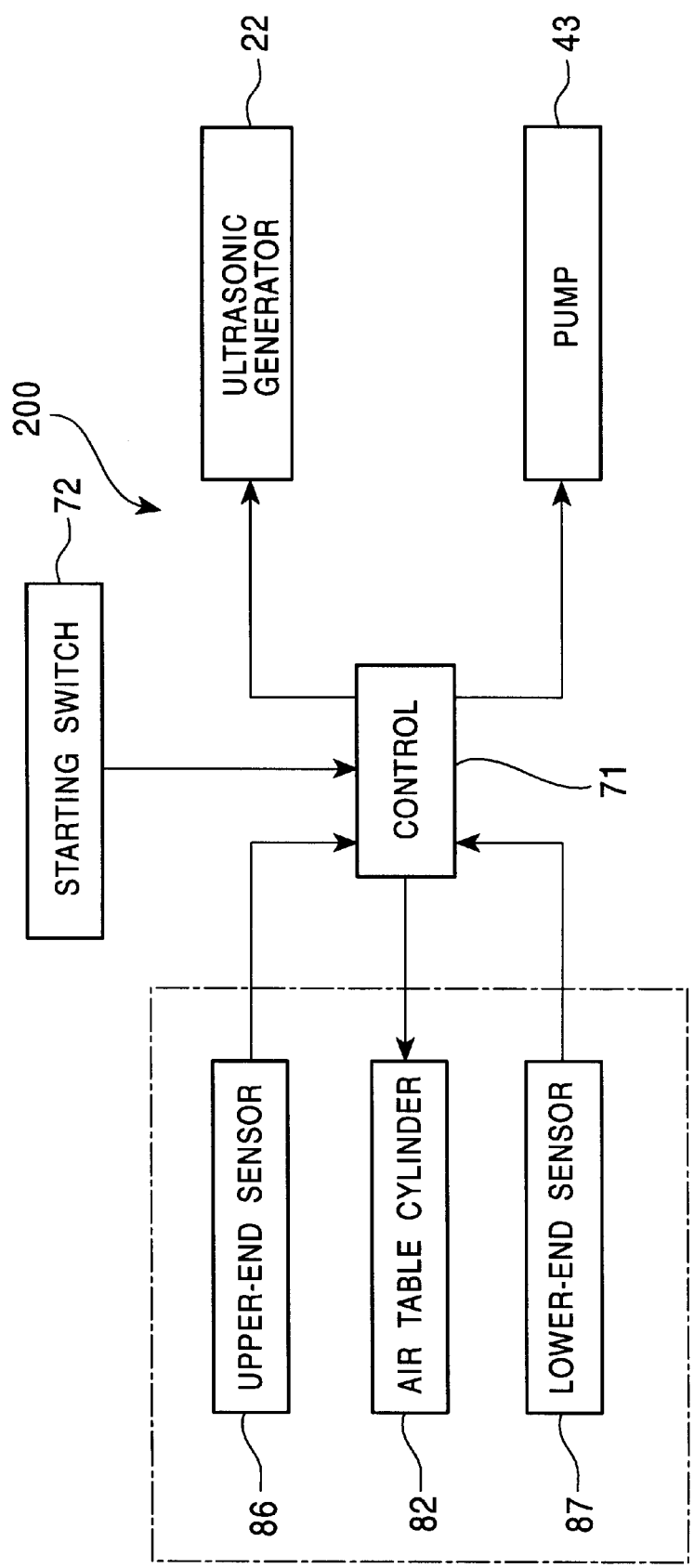
FIG. 12 shows a control block diagram of the apparatus shown in FIG. 11.

FIG. 12 shows an example of a control block diagram of the apparatus for recovering metal reflective films 200 shown in FIG. 11, and the control 71 is connected to a starting switch 72, the upper-end sensor 86, the air table cylinder 82. the lower-end sensor 87, the ultrasonic generator 22, and the pump 43.

Next, the operation of the apparatus for recovering metal reflective films 200 shown in FIG. 11 and FIG. 12 will be described.

The control 71 lowers the air table cylinder 82 in response to the starting switch 72 and the signal of the upper-end sensor 86. The control 71 operates the ultrasonic generator 22 and the pump 43 in response to the signal of the lower-end sensor 87. After a predetermined period of time which is sufficient for the separation, the control 71 stops the ultrasonic generator 22 and elevates the air table cylinder 82. Upon receiving the signal from the upper-end sensor 86, the control 71 stops the pump 43 after a predetermined period of time which is sufficient for washing off the gold reflective layer 1b and the top-coat layer 1a that have restuck on the disk. The separated disks 1 are retrieved with the cleaning device 91 by an operator, and unseparated disks are mounted on the cleaning device 91. When the starting switch 72 is pressed by an operator, a series of operations are repeated.

The pump is in operation for a given period of time while the disk 1 is being separated in the ultrasonic cleaning bath 21 and while the separated disk is raised. By circulating water 11 during and after separation, the gold reflective layer 1b and the like which float or sink in water 11 after separating from the disk 1 are recovered by the mechanical filter 42. Unless the gold reflective layer 1b and the UV-curable resin top-coat layer 1a are recovered at an appropriate moment, the operation of recovering the whole reflective film may result in the separated gold reflective layer 1b being stuck on the disk 1. This deteriorates the recovery percentage of the whole reflective film and the like. By working the pump for a certain period of time, water 11 from the nozzle 45a washes off the gold reflective layer 1b stuck on the disk 1 and returns it into the ultrasonic cleaning bath 21, and thereby it is recovered by the mechanical filter 42.

In accordance with the operations described above, the separated gold reflective layer 1b can be efficiently recovered.

Next, with reference to FIG. 13 and FIG. 14, other embodiments of the present invention, which are modifications of the apparatus shown in FIG. 11, will be described.

Figure 13:
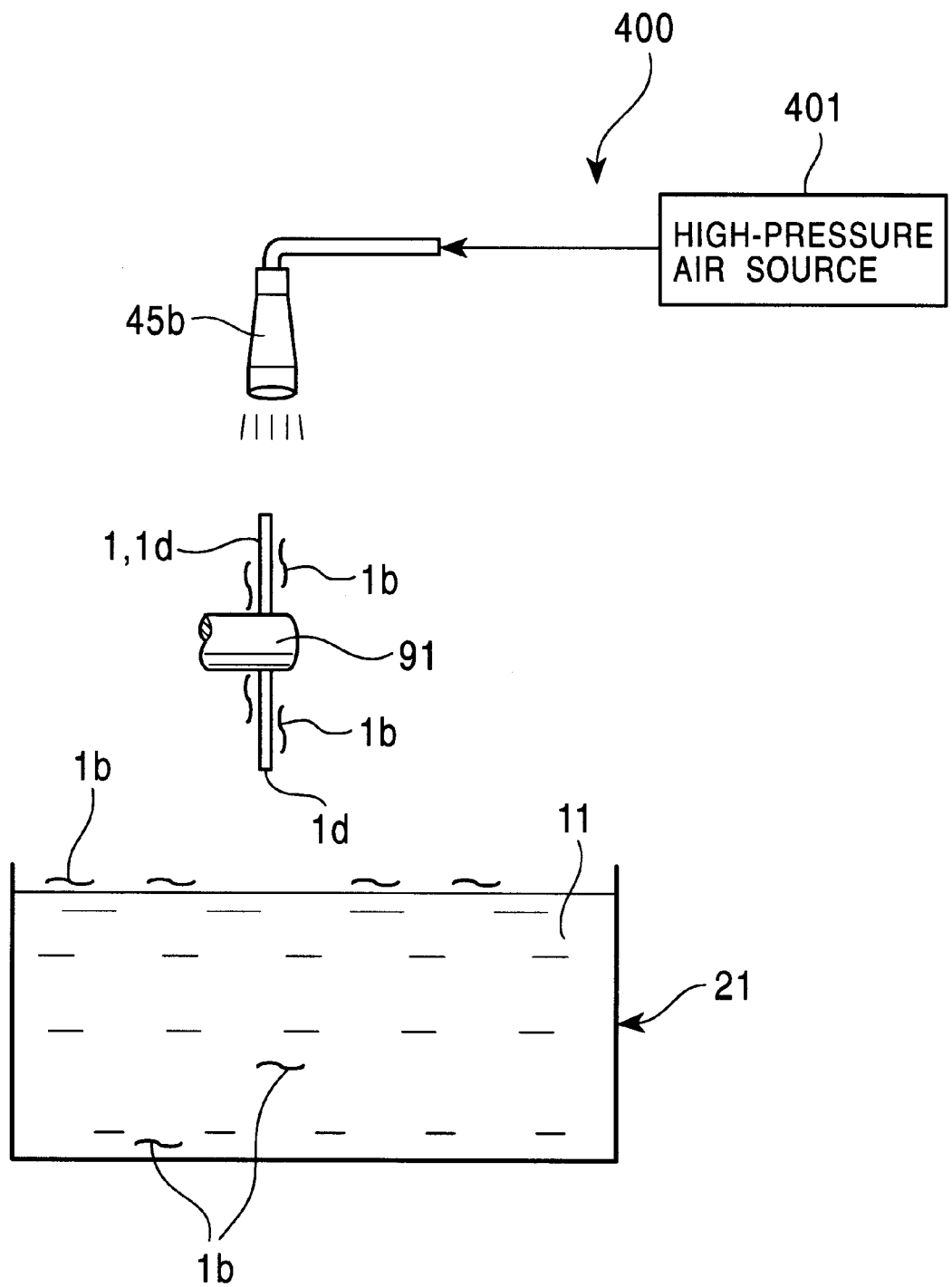
FIG. 13 shows an apparatus for recovering metal reflective films as an embodiment of the present invention.
Figure 14:
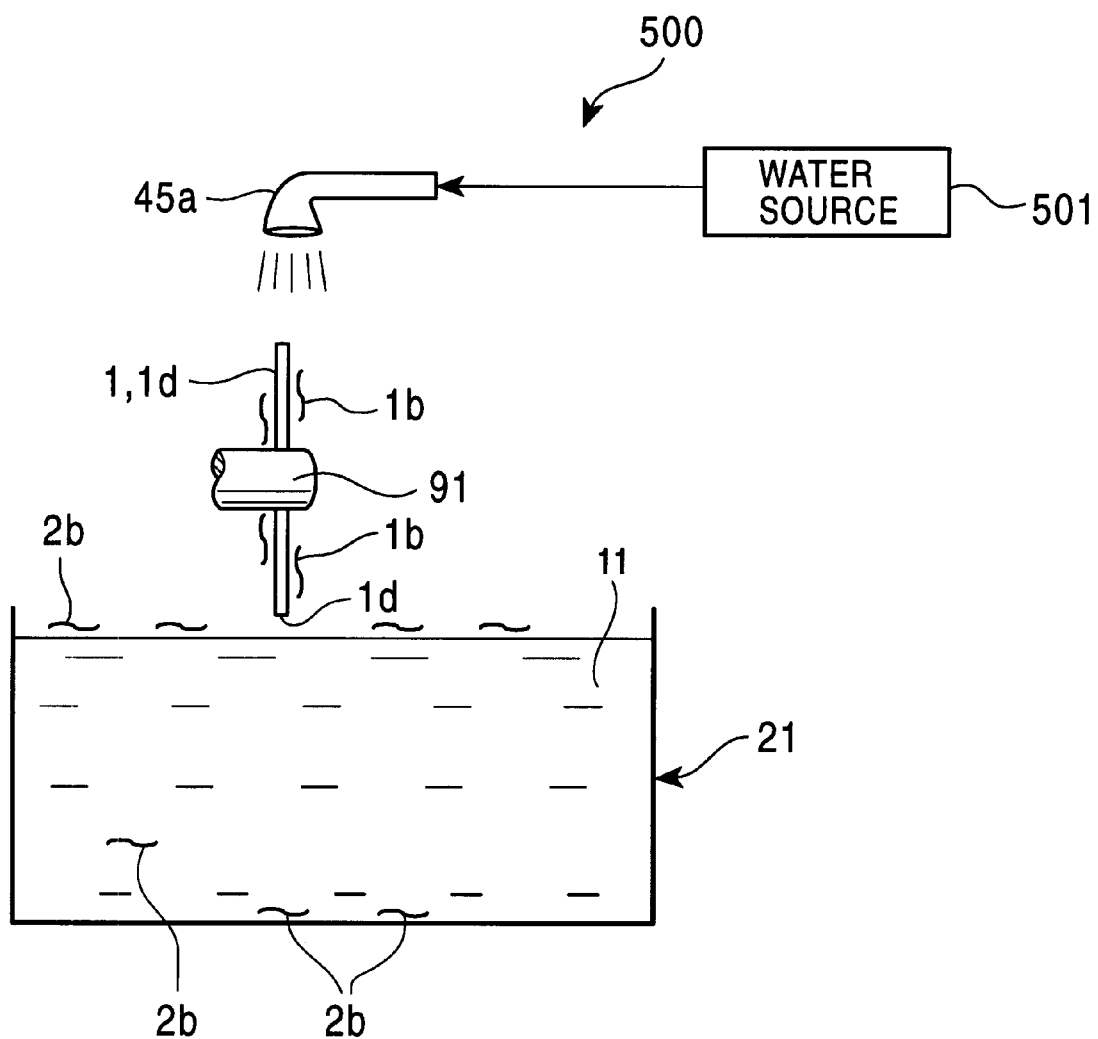
FIG. 14 shows an apparatus for recovering metal reflective films as an embodiment of the present invention.

FIG. 13 and FIG. 14 show fluid spray means 400 and 500 respectively. The fluid spray means 400 shown in FIG. 13 includes a high-pressure air source 401 and a nozzle 45b connected to the high-pressure air source 401. High-pressure air from the high-pressure air source 401 can be sprayed onto the disk 1 on the elevated cleaning device 91 through the nozzle 45b. Spraying of the high-pressure air makes the gold reflective layer 1b, which has been separated from the disk 1, but still sticks on the disk 1, fall from the polycarbonate substrate 1d of the disk 1 into water 11 in the ultrasonic cleaning bath 21.

The fluid spray means 500 shown in FIG. 14 includes a water source 501 and a nozzle 45a. Water from the water source 501 is sprayed onto the gold reflective layer 1b and the like which stick on the disk 1 mounted on the cleaning device 91, and the gold reflective layer 1b and the like are removed from the polycarbonate substrate 1d of the disk 1 and fall into water 11 in the ultrasonic cleaning bath 21 to be recovered.

Thereby, the gold refleotive layer 1b and the like restuck on the disk 1 can be securely recovered into water 11.

Also, a high-pressure, air flow and a water flow may be used at the same time.

Figure 15:
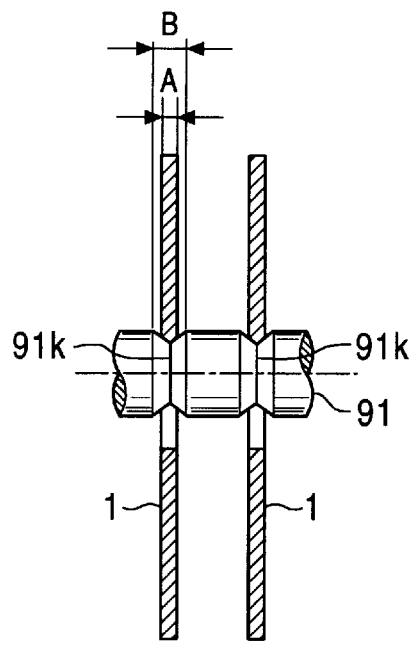
FIG. 15 shows an example of a cleaning device.
Figure 16:
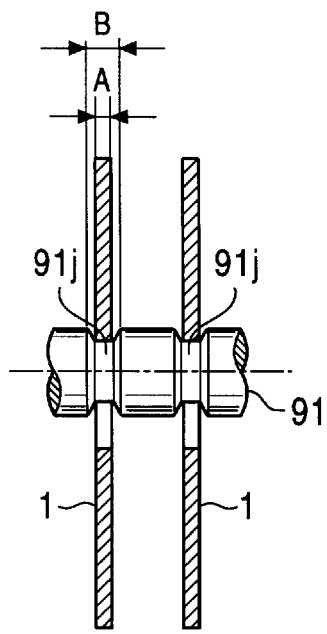
FIG. 16 shows an example of a cleaning device.
Figure 17:
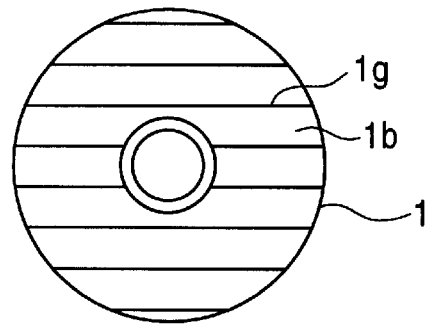
FIG. 17 shows a disk having a notched gold reflective layer.
Figure 18:
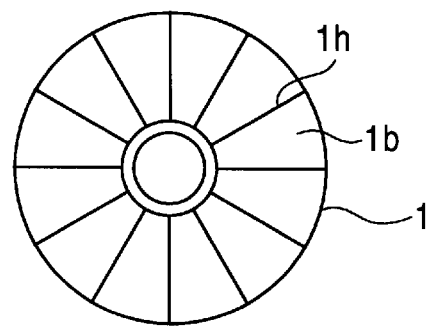
FIG. 18 shows a disk having a notched gold reflective layer.
Figure 19:
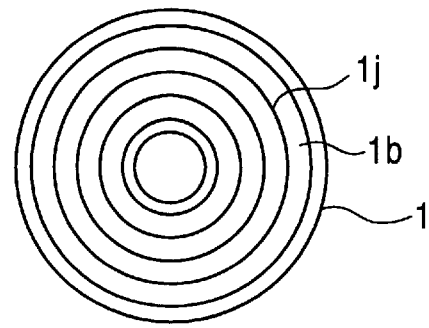
FIG. 19 shows a disk having a notched gold reflective layer.
Figure 20:
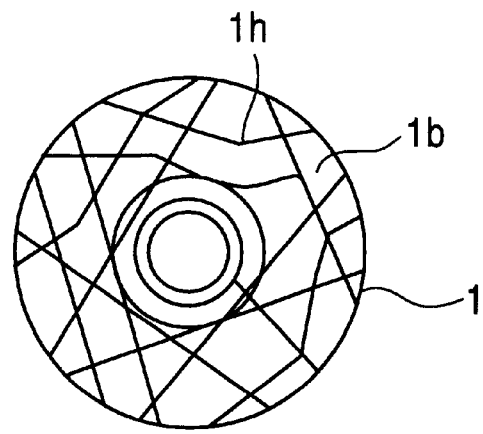
FIG. 20 shows a disk having a notched gold reflective layer.

FIG. 15 and FIG. 16 illustrate examples of the cleaning device 91 which is applicable to the embodiments shown in FIG. 4 and FIG. 11. A groove 91k of the cleaning device 91 shown in FIG. 15 is substantially v-shaped in cross section, and the maximum width B of the groove 91k is wider than the width of the disk 1.

A groove 91j shown in FIG. 16 is substantially trapezoidal in cross section, and the maximum width B of the groove 91j is wider than the width A of the disk 1.

The cleaning device 91 may have a groove which is semicircular or elliptic in cross section.

Next, FIG. 8 through FIG. 20 will be referred to.

FIG. 8 shows a notching means 600 for actively notching the gold reflective layer 1b and the UV-curable resin top-coat 1a. The notching means 600 is an apparatus for notching the gold reflective layer 1b and the UV-curable resin top-coat 1a in the disk 1 before recovering the substrate and the metal by means of the recycle apparatus 100 shown in FIG. 4 or the apparatus for recovering metal reflective films 200 shown in FIG. 11.

In accordance with the embodiments shown in FIG. 4 and FIG. 11, a used disk, a defective disk during production process, or an unused disk is mounted as it is on the cleaning device 91, and the gold reflective layer 1b and the UV-curable resin top-coat 1a in the disk 1 are separated and recovered.

On the other hand, the notching means 600 shown in FIG. 8 is used so that recovery efficiency of the substrate and the gold reflective layer in accordance with the recycle apparatus 100 shown in FIG. 4 or the apparatus for recovering metal reflective films 200 shown in FIG. 11 can be enhanced, by actively notching the gold reflective layer 1b and the UV-curable resin top-coat 1a, in advance, with patterns shown in FIGS. 9, 17, 18, 19 and 20.

The notching means 600 includes a positioning section 58, a setting plate 56, a supporting plate 57, two linear guides 53 and 53, and a metal mold 51.

The metal mold 51 is fixed on the bottom ends of the linear shafts 52 and 52 of the linear guides 53 and 53. Also the center of the metal mold 51 is fixed on a rod 55a of an air cylinder 55.

The disk 1 is positioned so that the gold reflective layer 1b and the UV-curable resin top-coat 1a beneath the label surface are opposed to the metal mold 51.

Several protruding portions 59 for making grooves are formed on the bottom surface of the metal mold 51. The protruding portions 59 are shaped such that the notch patterns shown in FIGS. 9, 17, 18, 19 and 20 are made on the label surface side of the disk 1.

The gold reflective layer 1b and the UV-curable resin top-coat 1a of the disk 1 illustrated in FIG. 9 have checkered notches 1f. The gold reflective layer 1b and the UV-curable resin top-coat 1a illustrated in FIG. 17 have parallel notches 1g. The gold reflective layer 1b and the UV-curable resin top-coat 1a illustrated in FIG. 18 have radial notches 1h. The gold reflective layer 1b and the UV-curable resin top-coat 1a illustrated in FIG. 19 have concentric notches 1j. The gold reflective layer 1b and the UV-curable resin top-coat 1a illustrated in FIG. 20 have random notches 1h.

When the cylinder 55 of the notching means 600 shown in FIG. 8 is in operation, the metal mold 51 moves downward in the Z1 direction along the linear guides 53 and 53, and thereby, patterns shown in FIGS. 9, 17, 18, 19 and 20 can be notched onto the gold reflective layer 1b and the UV-curable resin top-coat 1a on the label surface side of the disk 1.

As described above, by preliminarily making notches onto the gold reflective layer 1b and the UV-curable resin top-coat 1a with the protruding portions 59 (edges) of the metal mold 51, the separation and recovery of the gold reflective layer 1b can be performed in a shorter period of time by using the apparatus for recovering metal reflective films shown in FIG. 4 or FIG. 11.

Next, with reference to FIG. 21 through FIG. 24, other embodiments of apparatuses for recovering metal reflective films in accordance with the present invention will be described.

The embodiments shown in FIG. 21 through FIG. 24 are applicable to the recycle apparatus shown in FIG. 4 and the apparatus for recovering metal reflective films shown in FIG. 11.

Figure 21:
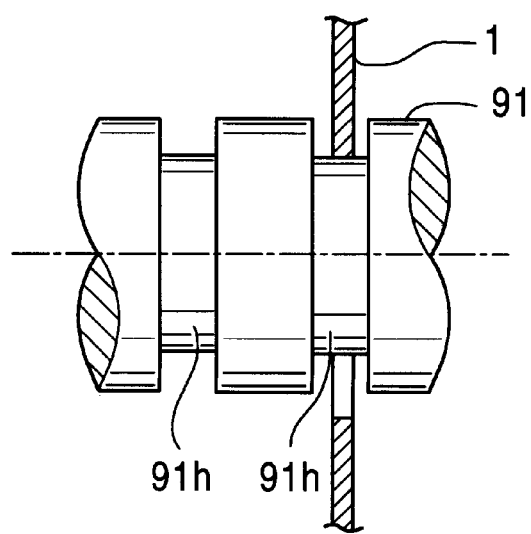
FIG. 21 shows a state in which a disk is fixed onto a cleaning device.

A cleaning device 91 shown in FIG. 21 has a plurality of grooves 91h at a given distance. Thus, the center holes of the disks 1 can be supported with the grooves 91h.

Figure 22:
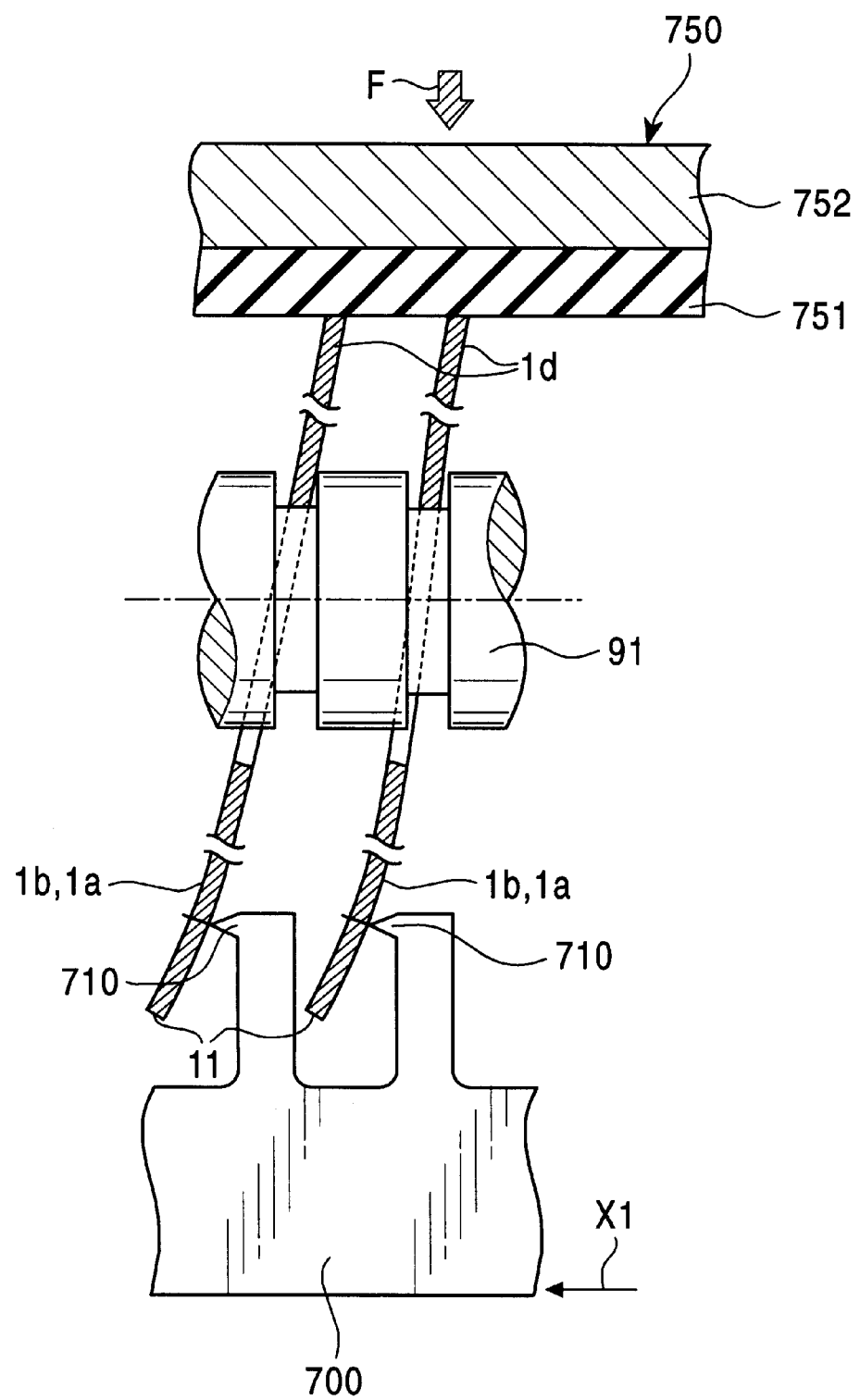
FIG. 22 Shows a state in which the disks fixed onto the cleaning device shown in FIG. 21 are notched.

FIG. 22 shows a state in which the gold reflective layer 1b of each disk 1 is notched with a notching device 700 as a notching means while the disk 1 is held with the cleaning device 91 shown in FIG. 21.

While the top end of the disk 1 is retained with a disk fixing device 750, the bottom end of the disk 1 can be notched by an edge 710 of the notching device 700. That is, as the notching device 700 moves in the X1 direction, the gold reflective layer 1b and the UV-curable resin top-coat 1a of each disk 1 are notched. At this stage, the top end of the disk 1 is elastically held with urethane rubber 751 on the disk fixing device 750. The urethane rubber 751 is fixed on steel 752. The disk fixing drive 750 presses the disk 1 downward with a force F. Thereby, the edge 710 makes a notch 1m as shown in FIG. 24 onto the gold reflective layer 1b and the UV-curable resin top-coat 1a.

Figure 24:
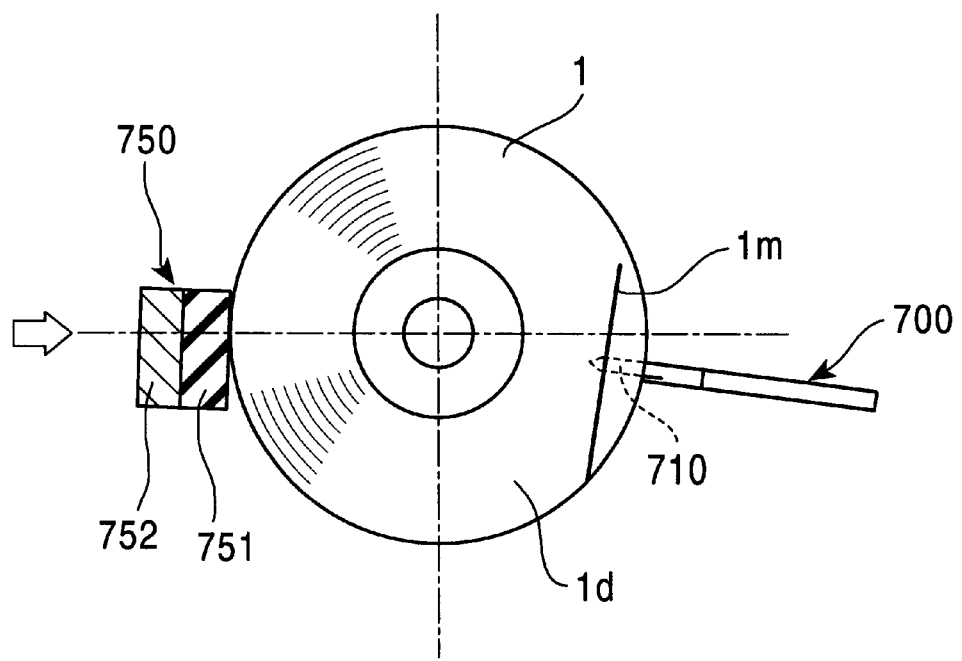
FIG. 24 shows a notching device and the like shown in FIG. 22.

By using the notching device 700 as a notching means shown in FIG. 22 and FIG. 24, there is no further need to preliminarily notch the gold reflective layer 1d and the UV-curable resin top-coat 1a by using the notching means 600 shown in FIG. 8.

Also, as shown in FIG. 6, FIG. 15, FIG. 16, and FIG. 22, if the cleaning device 91 is formed so as to hold a plurality of disks 1 at a given distance, the gold reflective layer separation can be performed to many disks at the same time with the disks not being in contact with each other. Besides, since water 11 as the medium flows between the adjacent disks, uneven separation does not easily occur. Preferably, the width of each groove is larger than the width of the disk so that the disk can rotate in response to water flow.

With regard to handling, for example, mounting and retrieving the disk 1 on and from the cleaning device 91, in accordance with the embodiments of the present invention. the mounting and retrieving are performed manually, however, the process may be automated by using a robot, a vacuum holding hand and the like.

Also, it may be possible to integrate notching into the apparatus during automatic transportation such that after notching the disk with the notching means 600 (notching mechanism) shown in FIG. 8, the notched disk is mounted on the cleaning device 91.

It is to be understood that the present invention is not limited to the embodiments described above.

In the embodiment shown in FIG. 14, water is used as the medium, however, another type of medium may be used as follows. Water, as the medium during ultrasonic radiation, does not necessarily have high purity, and may have additives as required. For example, by adding a surfactant into water, separation is accelerated, water is effectively drained after treatment, and reflective films are prevented from sticking to disks again. Also, there is no particular condition of temperature during ultrasonic radiation, and good results are obtainable at room temperature. Also, a mixture of water and another type of medium may be used instead of water. For example, a mixture of water and ethanol, and a mixture of water and methanol may be used. Also, although ultrasonic vibration from an ultrasonic generator is used in order to vibrate disks, other types of vibration generator may be employed. The groove for holding a disk may be substantially triangular in cross section.

The present invention is applicable not only to CDs (compact disks) and CD-Rs but also to other types of optical disks and magneto-optical disks, for example, digital video disks (DVDS) and laser disks (LDs).

In the embodiments shown in FIG. 4, FIG. 11 and the like, the disks 1, in parallel to each other, are substantially vertically retained with the cleaning device, however, the individual disks may be retained obliquely toward the vertical direction, or another retaining method may be used. Also, a single disk or a plurality of disks may be retained with the cleaning device.

Figure 23:
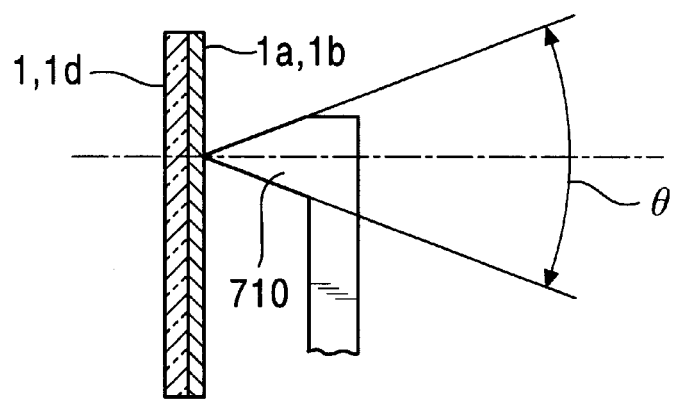
FIG. 23 shows an example of an edge on a notching device shown in FIG. 22.

Also, preferably, the edge 710 on the notching device shown in FIG. 23 has a sharp point, for example, with a point angle θ of 30 degrees so that deep notches are made by using stress concentration. Even in such a case, since the disks 1 bend, notches can be made by making use of springiness (elasticity). In such a case, the number of notches is, for example, two or less, and the width of the edges 710 on the notching device shown in FIG. 22 is, for example, 160 mm.

With respect to the metal reflective film, materials other than gold may be used depending on the types of disks.

What is claimed is:

1. A method of recycling a disk recording medium comprising the steps of:

retaining said disk recording medium in a liquid medium, said disk recording medium having a layered structure comprising a substrate, a dye layer, a reflective film, and a protective layer;

radiating ultrasonic waves onto said disk recording medium such that said substrate and said reflective film are separated from each other; and bringing a solution into contact with said substrate separated from said reflective film such that said dye layer is separated from said substrate in order to recover said substrate, said solution dissolving said dye layer.

2. A method of recycling a disk recording medium according to claim 1, further comprising the step of preliminarily notching said protective layer or said protective layer and said reflective film before said disk recording medium is irradiated with ultrasonic waves in order to separate said substrate and said reflective film from each other.

3. A method of recycling a disk recording medium according to claim 1, further comprising the step of heating said reflective film separated from said substrate such that a component of said protective film attached to said reflective film is vaporized.

4. A method of recycling a disk recording medium according to claim 1, further comprising the step of adding a solution for dissolving said dye layer onto said liquid medium before said disk recording medium is irradiated with ultrasonic waves in order to separate said substrate and said refleotive film from each other.

5. A method for recovering a metal reflective film, said metal reflective film being formed in a disk recording medium, said method comprising the steps of:

placing said recording medium in a liquid medium in a container;

applying vibration onto said recording medium placed in said liquid medium in order to separate said metal reflective film from said recording medium and to recover said metal reflective film into said liquid medium; and removing said separated metal reflective film in said liquid medium from said liquid medium.

6. A method for recovering a metal reflective film according to claim 5, wherein said vibration applied onto said recording medium is ultrasonic vibration.

7. A method for recovering a metal reflective film according to claim 5, further comprising the step of notching said recording medium before said vibration is applied onto said recording medium placed in said liquid medium.

8. A method for recovering a metal reflective film according to claim 5, further comprising the step of spraying fluid onto said recording medium after treatment for recovering said metal reflective film is performed to said recording medium and said recording medium is retrieved out of said liquid medium.

* * * * *

UNITED STATES PATENT AND TRADEMARK OFFICE
CERTIFICATE OF CORRECTION

PATENT NO. : 6,066,229
DATED : May 23, 2000
INVENTOR(S) : KOMINE et al.

It is certified that error appears in the above-identified patent and that said Letters Patent is hereby corrected as shown below:

Column 14, line 39, claim 4, line 6, "refleotive" should read --reflective- -.

Signed and Sealed this

Eighth Day of May, 2001

Attest:

NICHOLAS P. GODICI

Attesting Officer

Acting Director of the United States Patent and Trademark Office